United States Patent
Reiner

[11] Patent Number: 4,828,763
[45] Date of Patent: May 9, 1989

[54] THERAPEUTICALLY ACTIVE DERIVATIVES OF URSODEOXYCHOLIC ACID AND PROCESS FOR PREPARING THE SAME

[75] Inventor: Alberto Reiner, Como, Italy

[73] Assignee: Jago Research AG, Hergiswill, Switzerland

[21] Appl. No.: 121,258

[22] Filed: Nov. 16, 1987

[30] Foreign Application Priority Data

Nov. 26, 1986 [CH] Switzerland ................. 04728/86

[51] Int. Cl.$^4$ ............................................. C07J 1/00
[52] U.S. Cl. ....................................................... 260/397.1
[58] Field of Search ............................................ 260/397.1

*Primary Examiner*—Leonard Schenkman
*Assistant Examiner*—Joseph A. Lipovsky
*Attorney, Agent, or Firm*—Armstrong, Nikaido, Marmelstein, Kubovcik & Murray

[57] ABSTRACT

Thioesters of ursodeoxycholic acid of the formula:

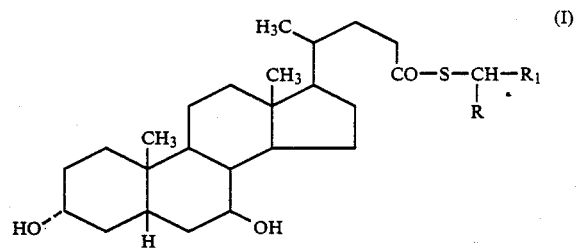

wherein R represents —H, —CH$_3$ or —COOH, and R$_1$ represents

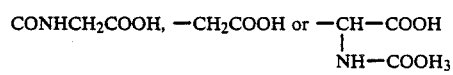

are useful in the treatment of altered biligenetic functions, lithiasis or dyskinesia of the biliary ducts. The esters are prepared by reacting the mixed anhydride of ursodeoxycholic acid with an alkyl or phenyl chloroformate with the appropriate mercaptan.

6 Claims, No Drawings

THERAPEUTICALLY ACTIVE DERIVATIVES OF URSODEOXYCHOLIC ACID AND PROCESS FOR PREPARING THE SAME

The present invention relates to derivatives of ursodeoxycholic acid, more particularly thioesters, and to a method for preparing such thioesters.

The compounds according to the present invention have the following structural formula:

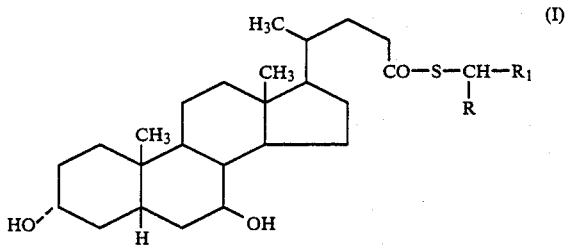

wherein R represents —H, —CH$_3$ or —COOH, and R$_1$ represents

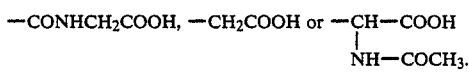

—CONHCH$_2$COOH, —CH$_2$COOH or —CH—COOH
                                                                    |
                                                                    NH—COCH$_3$.

The compounds of the present invention can be therapeutically employed in the treatment of altered biligenetic functions, lithiasis or dyskinesia of the biliary ducts.

Also within the scope of the present invention are the salts of thioesters of formula (I), either organic salts with aminoacids, such as lysine and arginine, or inorganic salts, such as the sodium, calcium, etc., salts.

It is also an object of the present invention to provide a process for preparing the compounds of formula (I). That process comprises two steps:

(a) preparing the mixed anhydride or ursodeoxycholic acid with an alkyl or phenyl chloroformate, and (b) esterifying the mixed anhydride with a reactive compound, containing the —SH group, preferably alpha-mercaptopropionylglycine and N-acetylcysteine.

In the first step of the process, the mixed anhydride of ursodeoxycholic acid is prepared by reacting the acid with an alkyl chloroformate, preferably ethyl, butyl or isobutyl chloroformate, or with phenyl chloroformate, in the presence of an organic amine, particularly triethylamine, at temperature between 6° and 20° C. The resulting mixed anhydride, in the form of a white heterogeneous material, is then reacted with the compound containing the —SH group, at temperature below 10° C. and in the presence of triethylamine. When the addition of triethylamine has been completed, the temperature of the reaction mixture is allowed to increase, due to the low heat reaction, to about 29° C.

The process of the present invention will now be explained by means of the following illustrative examples:

EXAMPLE 1

Ursodeoxycholic acid thioester with alpha-mercaptopropionylglycine (R=CH$_3$; R$_1$=—CO—NH CH$_2$ COOH).

To a solution of 19.6 g of ursodeoxycholic acid is 80 ml of dioxane, 4.75 ml of ethyl chloroformate are added and the solution is cooled to about 8° C. in an ice bath. One mole of triethylamine in dioxane (1:2.3 v/v) is slowly added, while maintaining the temperature between 8° and 10° C. A white heterogeneous material, not very fluid, slowly develops, and its fluidity increases as the material is heated to room temperature (about 19° C.).

To the material obtained above, 9.8 g of alpha-mercaptopropionylglycine at room temperature are added, and then the mixture is again cooled to about 8° C. Another mole of triethylamine in dioxane is slowly added, at a temperature always below 10° C. When the addition is completed, the temperature of the reaction mixture is allowed to increase spontaneously to about 19° C. The thioester formation reaction, which is a slow process requiring 7–10 hours, is slightly exothermic, and consequently the temperature of the reaction mixture increases to about 29° C.

The reaction product is separated by dilution with 500 ml of aqueous HCl, extraction with chloroform and washing with water. The chloroform phase is concentrated to a clear, colourless oil. Successive purification of the oil gives a white microcrystalline powder, m.p. 65°–70° C. (decomposes), soluble in cold alcohol and chloroform, and insoluble in water and acetone.

EXAMPLE 2

Ursodeoxycholic acid thioester with N-acetylcysteine

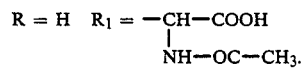

R = H    R$_1$ = —CH—COOH
                      |
                      NH—OC—CH$_3$.

To the mixed anhydride obtained according to the procedure of Example 1 starting with 10 g of ursodeoxycholic acid, 4.5 g of N-acetylcysteine at 20° C. are added, and the reaction mixture is cooled to a temperature of 7° C. One mole of triethylamine is then slowly added, while maintaining the temperature below 10° C. When the addition has been completed, the reaction mixture is heated to 20° C. and stirred to complete the reaction.

Following the procedure of Example 1, the product is obtained in form of a chromatographically pure, white microcrystalline powder, which decomposes at 57° C., but is totally liquid at 95°, and which is soluble in cold alcohol, partially soluble in acetone and insoluble in water.

I claim:

1. A thioester of ursodeoxycholic acid of the formula:

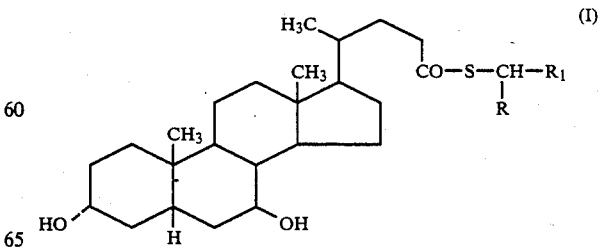

wherein R represents —H, —CH$_3$ or —COOH, and R$_1$ represents

—CONHCH₂COOH, —CH₂COOH or 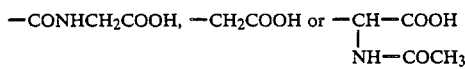

and pharmaceutically acceptable organic and inorganic salts thereof.

2. A thioester of ursodeoxycholic acid according to claim 1 wherein R is —CH₃ and $R_1$ is —CONHCH₂COOH.

3. A thioester of ursodeoxycholic acid according to claim 1 wherein R is H and $R_1$ is

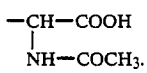.

4. A process for preparing a thioester of ursodeoxycholic acid of the formula:

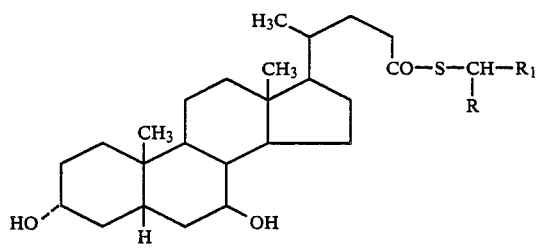

(I)

wherein R represents —H, —CH₃ or —COOH, and $R_1$ represents

—CONHCH₂COOH, —CH₂COOH or 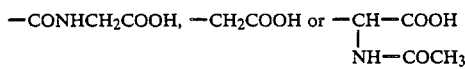

which comprises:
preparing a mixed anhydride of ursodeoxycholic acid with an alkyl or phenyl chloroformate at a temperature between 6 and 20° C. and in the presence of triethylamine, and
reacting the mixed anhydride with a compound of the formula

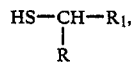

in the presence of triethylamine, wherein the triethylamine is added after the compound of the formula

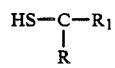

has been added and the temperature of the reaction mixture during the addition of the triethylamine does not exceed 10° C.

5. A process according to claim 4 wherein the alkyl chloroformate is ethyl, butyl or isobutyl chloroformate.

6. A process according to claim 4, wherein the preparation of the mixed anhydride is carried out in dioxane.

* * * * *